(12) United States Patent
Mingyan

(10) Patent No.: US 10,688,534 B2
(45) Date of Patent: Jun. 23, 2020

(54) AUTOMATED SILKWORM COCOON SEX SORTING

(71) Applicant: Hangzhou Canyu Technology Co., Ltd, Zhejiang (CN)

(72) Inventor: Zhao Mingyan, Zhejiang (CN)

(73) Assignee: Hangzhou Canyu Technology Co., Ltd, Zhejiang (CN)

( * ) Notice: Subject to any disclaimer, the term of this patent is extended or adjusted under 35 U.S.C. 154(b) by 259 days.

(21) Appl. No.: 15/973,763

(22) Filed: May 8, 2018

(65) Prior Publication Data

US 2018/0318884 A1 Nov. 8, 2018

(30) Foreign Application Priority Data

May 8, 2017 (CN) .......................... 2017 1 0331959

(51) Int. Cl.
*A01K 67/04* (2006.01)
*B07C 5/342* (2006.01)
*B07C 5/36* (2006.01)

(52) U.S. Cl.
CPC ............ *B07C 5/3422* (2013.01); *A01K 67/04* (2013.01); *B07C 5/36* (2013.01)

(58) Field of Classification Search
CPC ......... B07C 5/02; B07C 5/342; B07C 5/3422; B07C 5/3427; B07C 5/362; B07C 5/38; A01K 67/0333; A01K 67/04
See application file for complete search history.

(56) References Cited

U.S. PATENT DOCUMENTS

| 5,903,341 | A  | * | 5/1999  | Perry    | B07C 5/3422 |
|           |    |   |         |          | 209/587     |
| 6,520,311 | B1 | * | 2/2003  | Maeda    | B07C 5/02   |
|           |    |   |         |          | 198/339.1   |
| 7,737,379 | B2 | * | 6/2010  | Witdouck | B07C 5/342  |
|           |    |   |         |          | 209/588     |
| 9,180,464 | B2 | * | 11/2015 | Nimmo    | A01K 67/033 |
| 9,989,463 | B2 | * | 6/2018  | Skaff    | G01N 21/55  |
| 9,992,983 | B1 | * | 6/2018  | Sobecki  | B08B 3/045  |
| 2018/0077912 | A1 | * | 3/2018 | Comparat | A01K 67/033 |
| 2018/0318883 | A1 | * | 11/2018 | Mingyan | B07C 5/3422 |

FOREIGN PATENT DOCUMENTS

| CN | 105028347 A | * | 11/2015 | ............ A01K 67/04 |
| CN | 106198448 A | * | 12/2016 | |
| WO | WO-2017158216 A1 | * | 9/2017 | ............ A01K 67/033 |

OTHER PUBLICATIONS

English Translation of CN 105028347A; Inv: Zhao Mingyan; Pub. Date: Nov. 2015 (Year: 2015).*
English Translation of CN 106198448A; Inv: Yang et al.; Pub. Date: Dec. 2016 (Year: 2016).*

* cited by examiner

*Primary Examiner* — Joseph C Rodriguez
(74) *Attorney, Agent, or Firm* — Kunzler Bean & Adamson

(57) ABSTRACT

For sexing silkworm cocoons, a delivery mechanism carries a checker cocooning frame holding silkworm cocoons. A detection mechanism detects a female silkworm cocoon based on an optical wavelength emitted by the female silkworm cocoon. A sorting mechanism sorts the silkworm cocoons, putting female silkworm cocoons into a female collecting box, and male silkworm cocoons into a male collecting box.

16 Claims, 5 Drawing Sheets

AUTOMATED SILKWORM COCOON SEX SORTING

CROSS-REFERENCE TO RELATED APPLICATIONS

This patent application claims priority to Chinese Patent Application No. 201710331959.7 filed on May 8, 2017 for China Jiliang University, applicant and Zhao Mingyan, inventor, the entire contents of which are incorporated herein by reference for all purposes.

FIELD

The subject matter disclosed herein relates to silkworm cocoons sorting, and more specifically involves an apparatus for automatic sexing silkworm cocoons.

BACKGROUND

The quality of silk from silkworm cocoons varies by sex.

BRIEF SUMMARY

A fully-automatic apparatus for sexing silkworm cocoons is disclosed. The apparatus includes a delivery mechanism, a detection mechanism, and a sorting mechanism. The delivery mechanism comprises a checker cocooning frame that is carried and delivered by the delivery mechanism's conveyor belt to a dark box along the delivery route. The detection mechanism receives the checker cocooning frame transported by the delivery mechanism and determines the sex of the silkworm cocoons waiting to be sorted in the checker cocooning frame. The sorting mechanism sorts the silkworm cocoons waiting to be sorted according to the results coming from the detection mechanism. The female cocoons go into the female collecting box, while the male ones go into the male collecting box. The silkworm cocoon collecting mechanism includes female collecting mechanism and male collecting mechanism. The apparatus is high-efficiency, high-accuracy and low-cost.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION OF THE INVENTION

Figure 1:
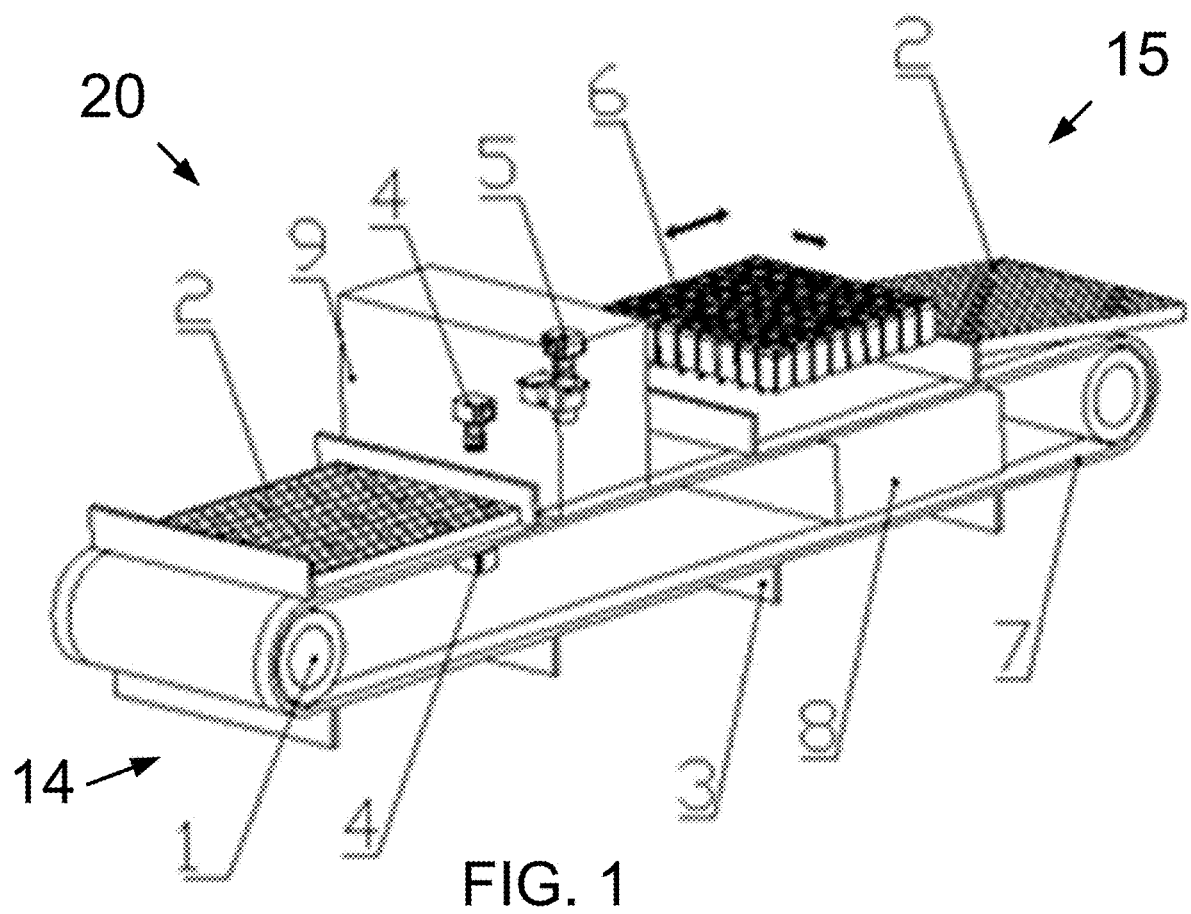
FIG. 1 is a perspective drawing showing one embodiment of a fully-automatic apparatus for sexing silkworm cocoons.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The description of elements in each figure may refer to elements of proceeding figures. Like numbers refer to like elements in all figures, including alternate embodiments of like elements.

The male cocoon silk quality is far superior to the female one, and the male cocoon silk can reduce the filaments of silk reeling. If male cocoon silk is used before the cocoon is boiled, it can greatly improve the quality of raw silk. However, there is no efficient, accurate, low cost male and female cocoon sorting machine in the market.

China's silk production of 640,000 to 650,000 tons of silk and silk production is stable at around 140,000 tons and 700 million meters, which is the world's largest. As people living standard improving, people's need for silk products (silk quilt, clothes, silk scarves, silk masks) is higher, especially in the European market with large demand for high-grade silk products.

The quality of the silk and silkworm cocoon of male and female have close relationships, the male silkworm silk having advantages like fine denier, friction resistance, clarity and good elasticity, which can be used to produce 6 A grade high-quality silk products, favored by the majority of consumers. However, the production of 6A raw silk in China is low and most of it is used for export, and the domestic and foreign markets are in short supply. It is impossible to choose a male cocoon without destroying the cocoon. So, there is a need for a machine to determine the sex of the silkworm cocoon and produce higher quality silk, improve production efficiency and ease the situation that the current market for high-grade silk products is in short supply.

On the market, there is an ultraviolet irradiation sexing machine, which can be used to select the cocoons by color, but this method is very harmful to the cocoon itself. In addition, there are machines using near infrared and X-ray equipment for analysis, although the accuracy is improved, but the near infrared spectrometer and X-ray detector are expensive, and often cannot be used by individual farmers.

The embodiments disclose a fully-automatic device for sexing silkworm cocoons with high-efficiency and high-accuracy, and low-cost, so that today's technical problem like the difficulty of sexing silkworm cocoons can be dealt, and the production of male raw silk can be promoted.

The technical solution of the invention is to provide a fully automatic cocoon sorting device with the following structure. The female cocoon includes a fluorescent protein gene after a gene editing technique that is used to detect the female cocoon.

The delivery mechanism comprises a checker cocooning frame that is carried and delivered by the delivery mechanism's conveyor belt to a dark box along the delivery route. The detection mechanism receives the checker cocooning frame transported by the delivery mechanism and determines the sex of the silkworm cocoons waiting to be sorted in the checker cocooning frame. The sorting mechanism sorts the silkworm cocoons waiting to be sorted according to the results coming from the detection mechanism. The female cocoons go into the female collecting box, while the male ones go into the male collecting box. The silkworm cocoon collecting mechanism includes a female collecting mechanism and a male collecting mechanism.

The female collecting mechanism may include the female recycling winding belt and a female collecting box. The female collecting box may sit below the female recycling winding belt as mentioned. The male collecting mechanism may include the male cocoon recycling winding belt and the male collecting box. The male collecting box may sit below the male cocoons recycling winding belt. The female winding belt and the male winding belt may be driven by a drive mechanism.

Optional, a cutting device is arranged on the bottom of female recycling winding belt and the male recycling winding belt. The cutting device's blade is close to the lower surface of the winding belt.

Optional, detection mechanism as mentioned includes the first module 4 and the second module with fluorescent recognition function. The first module as mentioned is in the former, the second module as mentioned is right after the first one. The first module detects grid straw cocooning frame plate for double cocoon and inferior cocoons, and determine their locations, the second module detects the female cocoons and male cocoons and determine their locations.

Optional, the sorting mechanism has integrated laser. The laser as described, cutting with straw cocooning frame case between the positioning of silk according to the position information of target silkworm cocoon, so that the target silkworm cocoon goes into corresponding collecting mechanism.

Optional, the sorting mechanism has electromagnetic hammer, and hit target silkworm cocoons according to the location data, so that these cocoons go into corresponding collecting mechanism.

Optional, the first module as mentioned is consist of normal charge-coupled device (CCD) cameras, while the second one consists of CCD cameras with fluorescent detection device.

Optional, the second module as mentioned runs machine vision programs to detect target cocoons, the female ones will release orange light, while male ones do not. The detection results are sent to sorting mechanism, then target cocoons are sorted and collected.

Optional, an illuminant is setting on the CCD camera. During the process of fluorescence detection, once silkworm chrysalises are under the 554 nanometer (nm) light, the fluorescent protein in female ones will release 586 nm light. The CCD camera can detect the fluorescent protein when implementing a cutoff fluorescent filter whose central wavelength is 586 nm. The optical design of this mechanism is that: using CREE CXA2530, high power LED bubbles implementing with 554 central wavelength cutoff fluorescent filters, the filters are used to keep the purity of the illuminant. When light hits on the dichroic mirror, it then is reflected to the silkworm chrysalis, and CCD camera detects the silkworm chrysalis through dichroic mirror.

Optional, pictures are taken by the CCD camera, and analyzed by image processing algorithm to separate silkworm chrysalises by genders. With the MYSQL data being built, silkworm cocoons can be cut by laser and fall into corresponding collecting box by the control of the single chip.

This invention, compared to today's technology, has these merits: 1. Combining the bio fluorescent protein technology with the machine vision technology, the special wavelength filter is added to the camera and the light source to eliminate the interference of the non-excited light wave long light, so as to realize the accurate and high-speed recognition of the male and female cocoon. 2. In order to reject the traditional physical and contact method of picking cocoons, the CO2 laser cutting technology is adopted to carry out the single laser rectification and coupling, and the fiber is conducted from the fiber to the laser head, and the precise and high speed picking is carried out to the male and female cocoons, so as to avoid the damaged square plate and cocoon.

The Figures include: belt pulley 1; a checker cocooning frame 2; silkworm cocoons 2-1; targeted raw silk 2-2; Silkworm chrysalis 2-3; a crosswise guide plate 3 of the checker cocooning frame 2; a normal CCD camera 4; a fluorescent detection system 5; a lamp bead 5-1; a green fluorescent filter 5-2; a dichroic mirror 5-3; an orange fluorescent filter 5-4; CCD camera 5-5 with fluorescent detection function; an integrated laser 6; a laser beam 6-1; a laser cutting trajectory 6-2; a conveyor belt 7; a cocoon collecting box 8; a dark box 9; a lengthways guide plate 10 of the checker cocooning frame 2; a cocoon collecting mechanism 11; a female cocoon recycling winding belt 11-1; a female cocoon collecting box 11-2; male cocoon recycling winding belt 11-3; a male cocoon collecting box 11-4; and an electromagnetic hammer 12.

The following is a detailed description of the embodiments of the invention, but the present invention is not limited to these embodiments. The present invention covers any substitution, modification, equivalent method and scheme for the spirit and scope of the invention.

In order to make the public know about this invention has a thorough, detailed in the following the invention optimization example illustrates the specific details, and those skilled in the art can fully understand the invention.

Refer to the attached drawings in the following paragraphs for a more specific description of the invention. It should be noted that the attached drawings are both in a simplified form and use non-precise proportions, which are only used to facilitate and clarify the purpose of the embodiment of the invention.

Figure 2:
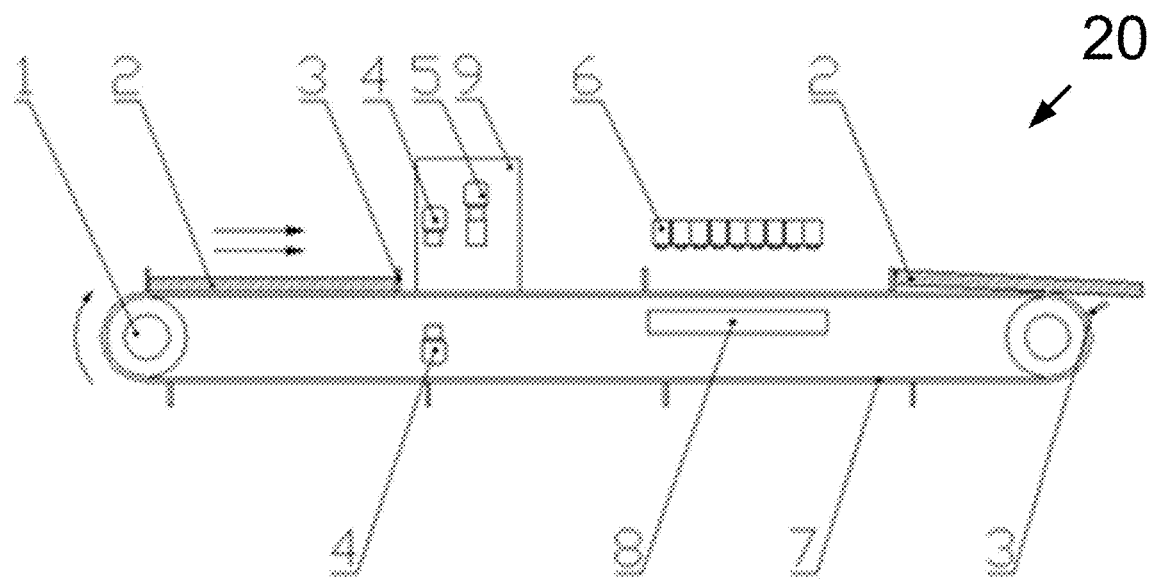
FIG. 2 is a side view drawing showing one embodiment of a fully-automatic apparatus for sexing silkworm cocoons.

FIGS. 1 and 2 shows the structure of the full-automatic apparatus 20 for sexing cocoons, including a delivery mechanism 14, a detection mechanism 5, and a sorting mechanism 15.

The delivery mechanism 14 carries a checker cocooning frame 2 holding silkworm cocoons. The checker cocooning frame 2 is carried and delivered by the delivery mechanism's conveyor belt 7 as mentioned to the dark box 9 along the delivery route.

The detection mechanism 20 detects a female silkworm cocoon 2-1 based on an optical wavelength emitted by the female silkworm cocoon 2-1. The detection mechanism 20 may be located in the upper place of the dark box 9. When the checker cocooning frame 2 is transported to the detection mechanism 20 by the delivery mechanism 14, the detection mechanism 20 will sex the silkworm cocoons 2-1 waiting to be sorted in the checker cocooning frame 2.

The sorting mechanism 15 sorts the silkworm cocoons 2-1, putting female silkworm cocoons 2-1 into a female collecting box 11-2, and male silkworm cocoons 2-1 into a male collecting box 11-4. The sorting mechanism 15 sorts the silkworm cocoons 2-1 waiting to be sorted according to the results coming from the detection mechanism 20. The female cocoons 2-1 go into the female collecting box 11-2, while the male cocoons 2-1 go into the male collecting box 11-4.

The detection mechanism 20 comprises a second CCD camera that detects the optical wavelength emitted by the female silkworm cocoon 2-1. The detection mechanism 20 may include a first module and a second module with fluorescent recognition function (fluorescent detection system).

The first module detects grid straw cocooning frame plate of the checker cocooning frame 2 for double cocoon 2-1 and inferior cocoons 2-1 and determines their locations. The second module detects the female cocoons 2-1 and male cocoons 2-1 and determines their locations. The second module is inside the dark box, and the first module is outside the dark box.

The sorting mechanism 15 may include an integrated laser 6. The laser 6 may cut with straw cocooning frame case of the checker cocooning frame 2 between the positioning of silk according to the position information of target silkworm cocoon 2-1, so that the target silkworm cocoon 2-1 goes into corresponding collecting mechanism.

The checker cocooning frame 2 is placed in the starting position, the crosswise guide plate 3 of the checker cocooning frame 2 accurately positions the checker cocooning frame 2. The conveyor belt 7 moves and the checker cocooning frame 2 enters the dark box 9. A visible light CCD camera 4 finds the double cocoons 2-1 and disqualified cocoons 2-1 and determines their locations. The fluorescent detection system 5 determines the location of male and female cocoons 2-1. When checker cocooning frame 2 moves under the integrated laser 6 and the laser head 6 operates, the double cocoons 2-1, the disqualified cocoons 2-1, the female cocoons 2-1, and the male cocoons 2-1 are picked in turn. The cocoon collecting box 8 collects the cocoons 2-1. After sorting, the conveyor belt 7 carries the checker cocooning frame 2 to move forward, and then fall into the checker cocooning frame container (not shown). The cocoon collecting box 8 may move beneath the integrated laser, carrying double cocoons 2-1, disqualified cocoons 2-1, female cocoons 2-1, and male cocoons 2-1.

Figure 3:
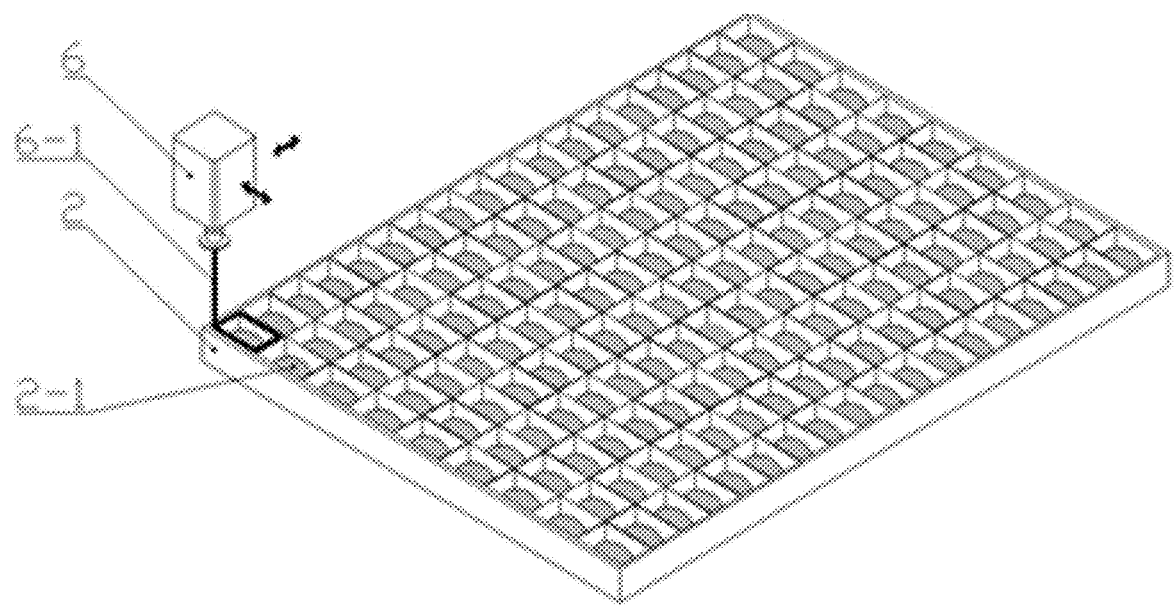
FIG. 3 is a perspective drawing showing one embodiment of an integrated laser and checker cocooning frame.
Figure 4:
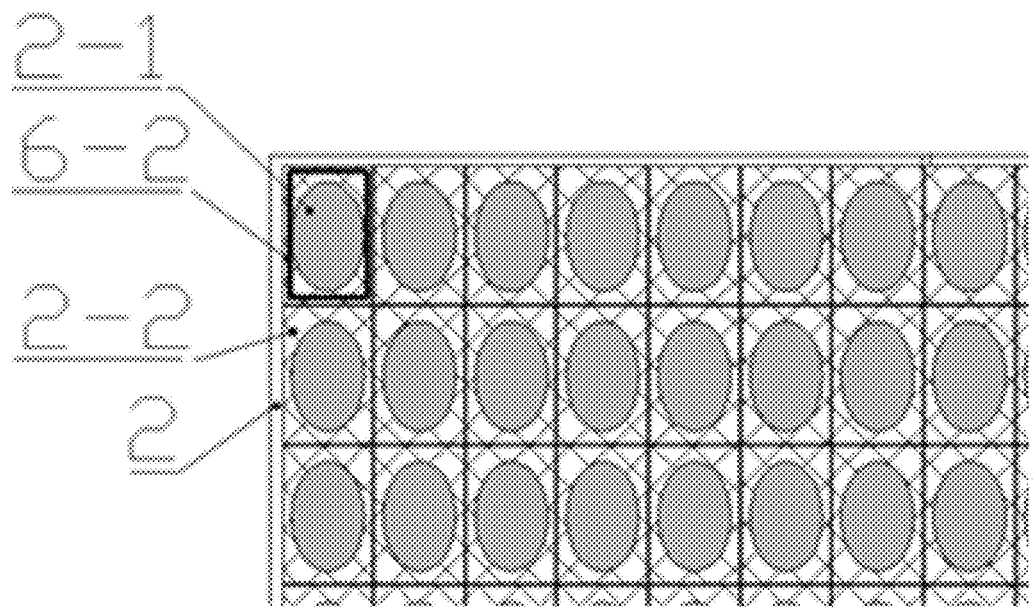
FIG. 4 is a top view drawing showing one embodiment of an integrated laser and checker cocooning frame.

FIGS. 3 and 4 shows the integrated laser 6 cutting off the cocoons from the checker cocooning frame 2. Laser cutting is extremely quick and is able to avoid the destruction to the checker cocooning frame 2. According to China's national standard, the checker cocooning frame 2 has two standards, 12*13=156 grids and 9*18=162 grids. We apply this standard, have 156 or 162 integrated lasers. When selecting cocoons, the laser 6 above the target cocoons will be wired, and the laser beam 6-1 will be formed. The laser will move horizontally, moving along the cutting route 6-2, cutting the targeted raw silk 2-2, so that silkworm cocoon 2-1 can come out of the checker cocooning frame 2.

Figure 5:
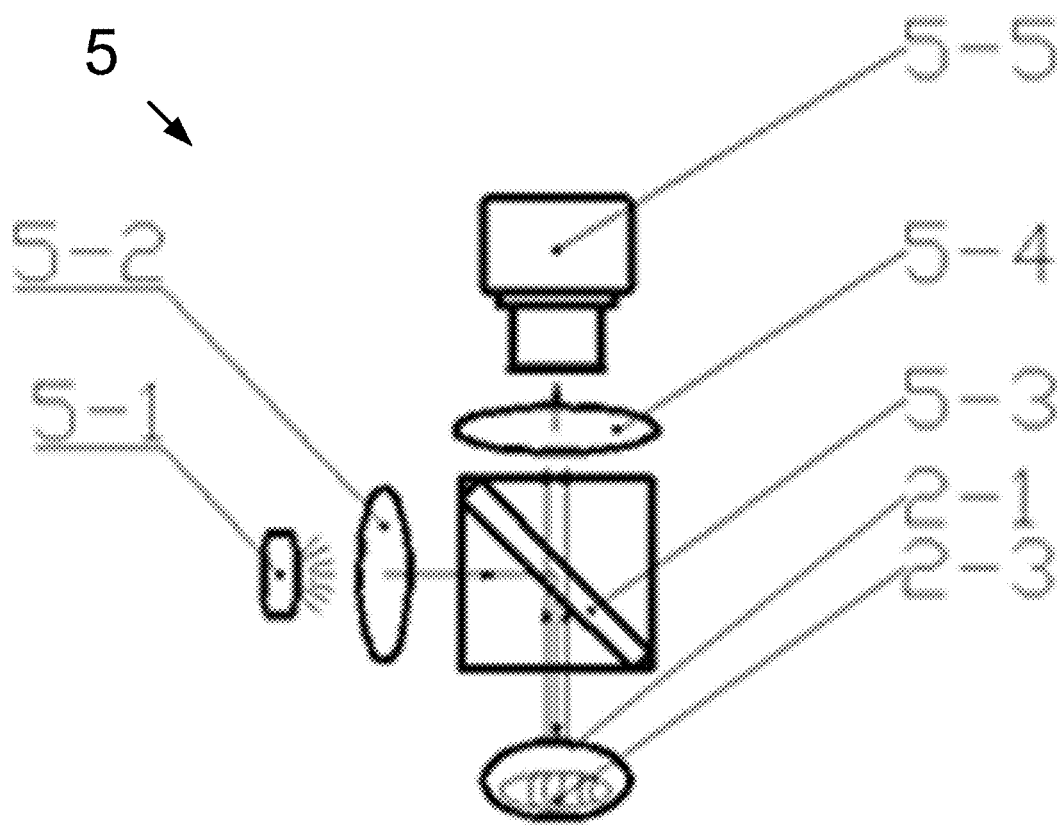
FIG. 5 is a side view drawing showing one embodiment of a detection mechanism.

FIG. 5 shows the structure of the second module. A female silkworm chrysalis/cocoon can express orange fluorescence throughout its life cycle. After the light from the LED 5-1 goes through green fluorescence filter 5-2, the light turns into green right with the 554 nanometer (nm) central wave length and a 30 nm band width. When the green light hits on the dichroic mirror 5-3 and reflects to the silkworm cocoon 2-1. The green light stimulates the female silkworm cocoon to emit an orange 586 nm light, which is transmitted through the dichroic mirror and the orange fluorescence filter and detected by the second CCD camera to identify the female silkworm cocoon. The orange fluorescence filter 5-4 has 586 nm central length, and 20 nm band width, which filters out other wave-length-light's interruption and only let the light with 576 nm to 596 nm wave lengths. The CCD camera 5-5 for fluorescence detection can detect the light with 576 nm to 596 nm wave length to determine the sex of the silkworm cocoon 2-1. Therefore, machine vision recognition technology and lighting filters and other devices, fast detection of genders of silkworm cocoons 2-1 can be achieved.

Images from the second CCD camera 5-5 images are analyzed by an image processing algorithm and database to separate the silkworm cocoons 2-1 by sex. In one embodiment, the images are analyzed by image processing algorithm to separate silkworm cocoons 2-1 by genders. A database such as a MYSQL database may sort silkworm cocoons 2-1 under the control of a controller or single chip.

Figure 6:
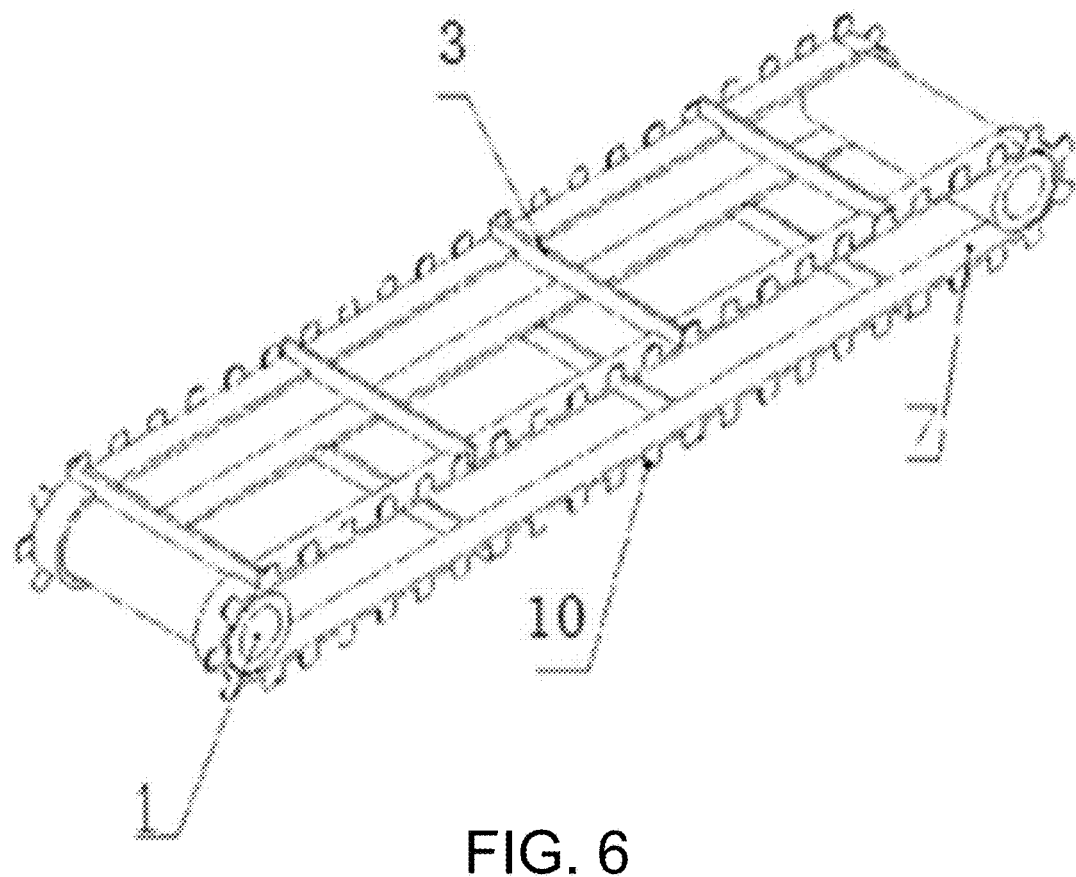
FIG. 6 is a perspective drawing showing one embodiment of a delivery mechanism.

FIG. 6 shows the structure of the delivery mechanism 14. The checker cocooning frame 2 waiting to be sorted is put into the conveyor belt 7 at the beginning position A, and move through following positions respectively, detection position B, sorting position C, the checker cocooning frame falling position D. The distance between two the crosswise guide plates 3 of the checker cocooning frame 2 is exact the same of the length of the checker cocooning frame 2. On the two conveyor belts 7 there sit lengthways guide plates 10 of the checker cocooning frame 2. The distance between lengthways guide plates 10 is the same of the width of the checker cocooning frame 2. With the help of these four plates, the checker cocooning frame 2 can be an exact position to make sure the movements are accurate. There are multiple lengthways guide plates 10, to make sure the checker cocooning frame 2 is in perfect position in the length direction. There are at least three plates on each side of the checker cocooning frame 2. Two conveyor belts 7 must be synchronous, so that any slips of the checker cocooning frame 2 are avoided.

The embodiments are a mechanical and electrical integration work that integrates functions of machine vision and intelligent sorting. The embodiments are able to detect and sort out disqualified cocoons 2-1 quickly and accurately and allow fast and accurate sexing to be achieved. There are two detailed points about this: 1. Combining the bio fluorescent protein technology with the machine vision technology, the special wavelength filter is added to the camera and the light source to eliminate the interference of the non-excited light wave long light, so as to realize the accurate and high-speed recognition of the male and female cocoon. 2. In order to reject the traditional physical and contact method of picking cocoons 2-1, $CO_2$ laser cutting technology is adopted to carry out the single laser rectification and coupling, and the fiber is conducted from the fiber to the laser head, and the precise and high-speed picking is carried out to the male and female cocoons 2-1, so as to avoid damaging square plates and cocoons 2-1.

Figure 7:
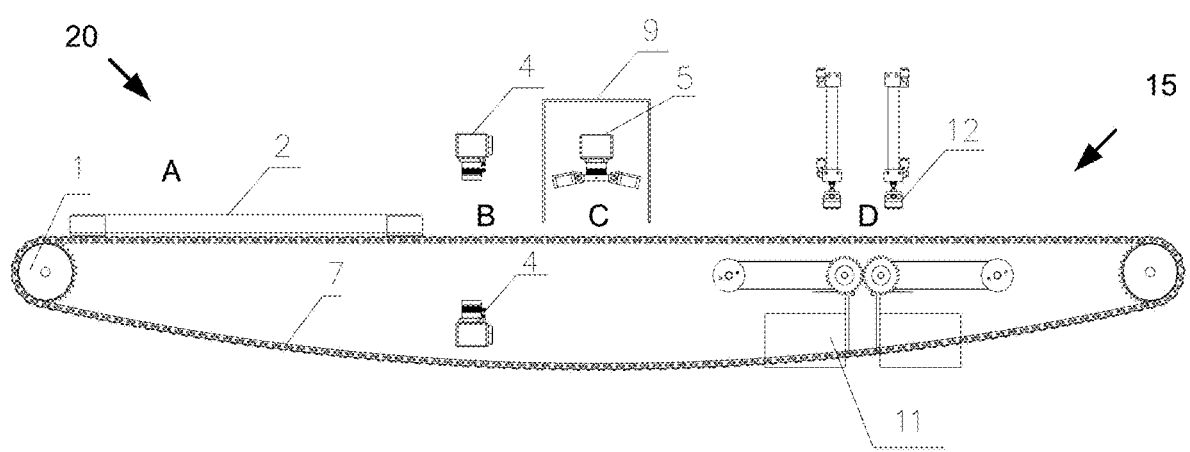
FIG. 7 is a side view drawing showing one embodiment of a delivery mechanism.

FIG. 7 shows another method of this automatic device. Compared to the device of FIG. 6, there are two differences. First, there is an alternate collecting mechanism 11. Second, there is an alternate embodiment of the sorting mechanism 15. Additional details are shown in FIG. 8.

Figure 8:
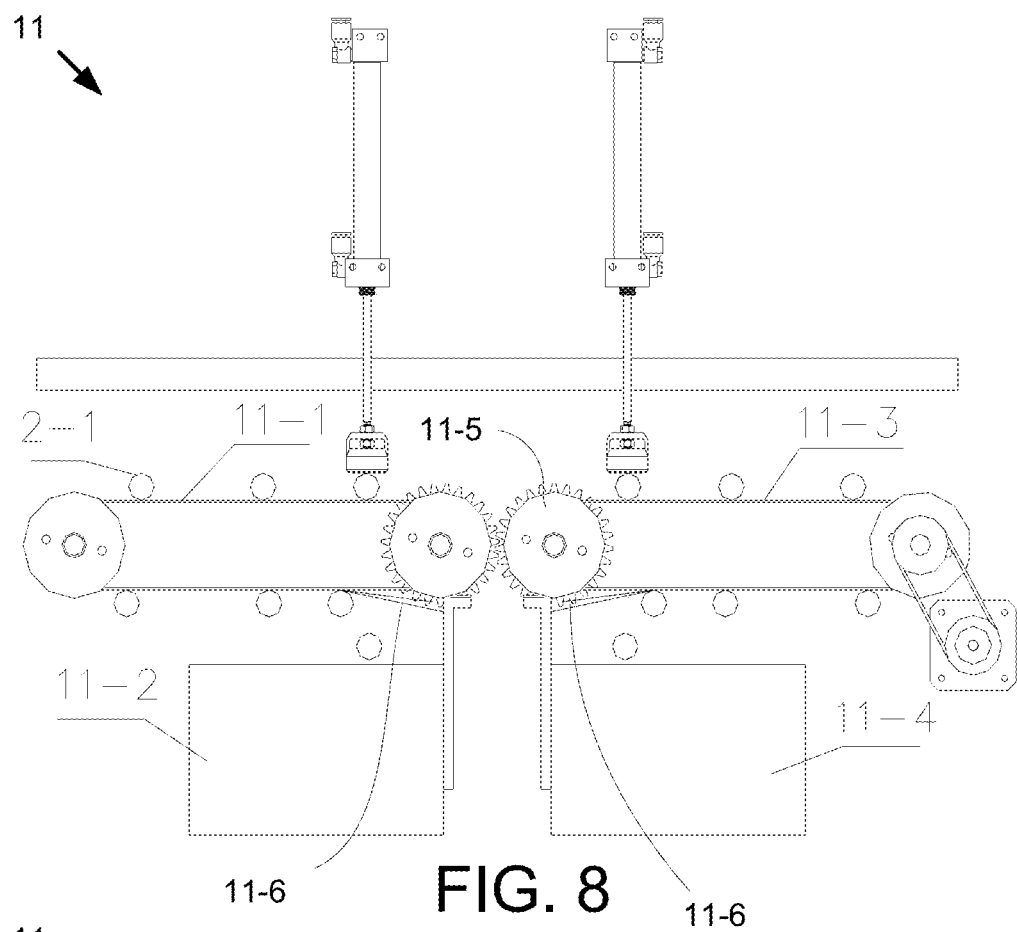
FIG. 8 is a side view drawing showing one embodiment of a collecting mechanism.

FIG. 8 illustrates one embodiment of the sorting mechanism 15. The sorting mechanism 15 may include a female recycling mechanism and a male recycling mechanism, the female recycling mechanism comprising a female recycling winding belt 11-1 with a cutting device 11-6 disposed close to the lower surface of the female recycling winding belt 11-1 that cuts each female cocoon 2-1 from the female recycling winding belt 11-1 into the female collecting box 11-3. The male recycling mechanism may include a male recycling winding belt 11-3 with a cutting device 11-6 disposed close to the lower surface of the male recycling winding belt 11-3 that cuts each male cocoon 2-1 from the male recycling winding belt 11-2 into the male collecting box 11-4. The female recycling winding belt 11-1 and the male recycling winding belt 11-3 are driven by a drive mechanism such as gears 11-5. The driving mechanism may include two pair of gears 11-5, on the shaft with has female recycling winding belt pulley and the shaft with male pulley, meshed gears 11-5 are set to control the direction of recycling winding belts 11-1/11-3. Sorting may be achieved by electromagnetic hammer 12. The electromagnetic hammers 12 may push the silkworm cocoons 2-1 from the checker cocooning frame 2 according to the position information of each silkworm cocoon 2-1, so that each male silkworm cocoon 2-1 goes into the male collecting box 11-4 and each female silkworm cocoon 2-1 goes into the female collecting box 11-4.

Figure 9:
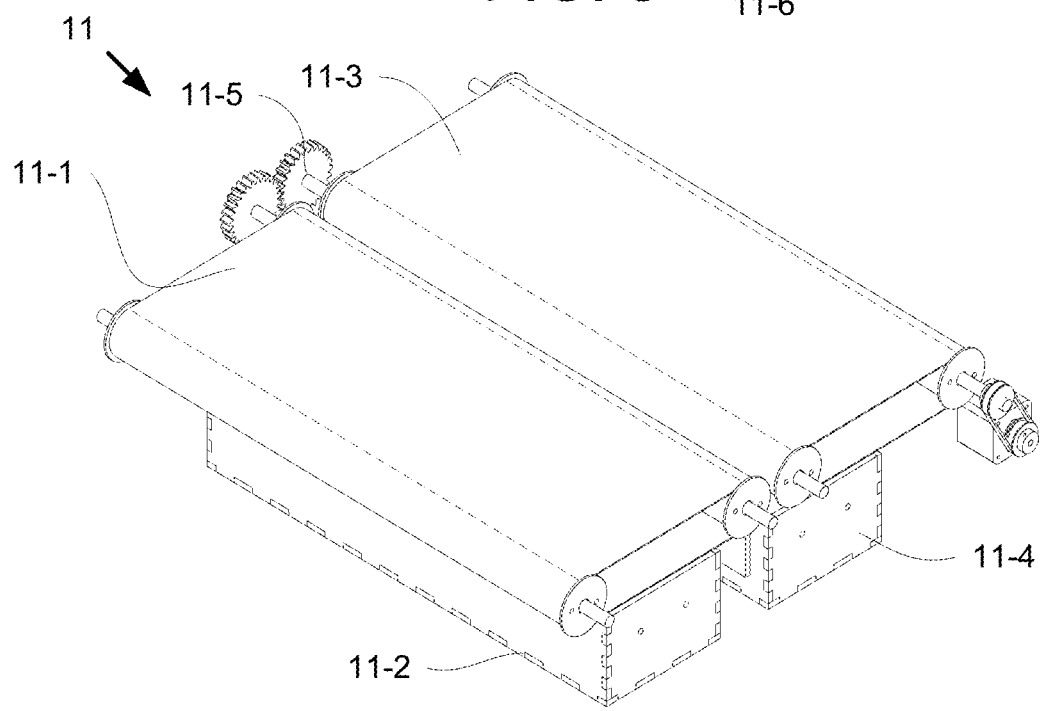
FIG. 9 is a perspective drawing showing one embodiment of a collecting mechanism.

FIG. 9 shows a perspective view different angles of the collecting mechanism 11 of FIGS. 7 and 8.

The above way of implementation does not constitute a limitation on the protection scope of the technology scheme. Any modification, replacement or improvement within the spirit and principles of the above methods shall be included in the protection of the technology scheme.

What is claimed is:

1. An apparatus comprising:
    a delivery mechanism that carries a checker cocooning frame holding silkworm cocoons;
    a detection mechanism that detects a female silkworm cocoon based on an optical wavelength emitted by the female silkworm cocoon, the detection mechanism comprising a light emitting diode (LED), a green fluorescence filter, a dichroic mirror, wherein light from the LED goes through the green fluorescence filter producing a green light with a 554 nm central wave length and 30 nm bandwidth that is refracted by the dichroic mirror on to the silkworm cocoon, and wherein light from the silkworm cocoon is transmitted through the dichroic mirror passing through an orange fluorescence filter with a 586 central length and a 20 nm bandwidth to a first CCD camera; and
    a sorting mechanism that sorts the silkworm cocoons, putting female silkworm cocoons into a female collecting box, and male silkworm cocoons into a male collecting box.

2. The apparatus of claim 1, wherein the detection mechanism comprises the first charge-coupled device (CCD) camera that detects the optical wavelength emitted by the female silkworm cocoon.

3. The apparatus of claim 1, wherein the green light stimulates the female silkworm cocoon to emit an orange 586 nm light, which is transmitted through the dichroic mirror and the orange fluorescence filter and detected by the first CCD camera to identify the female silkworm cocoon.

4. The apparatus of claim 1, wherein images from the first CCD camera are analyzed by an image processing algorithm and database to separate the silkworm cocoons by sex.

5. The apparatus of claim 2, wherein the detection mechanism comprises a second CCD camera that identifies a grid straw cocooning frame plate of the checker cocooning frame, position information for each silkworm cocoon, double cocoons, and inferior cocoons within the grid straw cocooning frame plate.

6. The apparatus of claim 5, wherein the sorting mechanism comprises a plurality of integrated lasers that cut the silkworm cocoons from the checker cocooning frame according to the position information of each silkworm cocoon, so that each male silkworm cocoon goes into the male collecting box and each female silkworm cocoon goes into the female collecting box.

7. The apparatus of claim 5, wherein the sorting mechanism comprises a plurality of electromagnetic hammers that push the silkworm cocoons from the checker cocooning frame according to the position information of each silkworm cocoon, so that each male silkworm cocoon goes into the male collecting box and each female silkworm cocoon goes into the female collecting box.

8. The apparatus of claim 5, wherein the sorting mechanism comprises a female recycling mechanism and a male recycling mechanism, the female recycling mechanism comprising a female recycling winding belt with a cutting device disposed close to the lower surface of the female recycling winding belt that cuts each female cocoon from the female recycling winding belt into the female collecting box, the male recycling mechanism comprising a male recycling winding belt with a cutting device disposed close to the lower surface of the male recycling winding belt that cuts each male cocoon from the male recycling winding belt into the male collecting box.

9. A system comprising:
    a dark box;
    a delivery mechanism that carries a checker cocooning frame holding silkworm cocoons;
    a detection mechanism that detects a female silkworm cocoon in the dark box based on an optical wavelength emitted by the female silkworm cocoon, the detection mechanism comprising a light emitting diode (LED), a green fluorescence filter, a dichroic mirror, wherein light from the LED goes through the green fluorescence filter producing a green light with a 554 nm central wave length and 30 nm bandwidth that is refracted by the dichroic mirror on to the silkworm cocoon, and wherein light from the silkworm cocoon is transmitted through the dichroic mirror passing through an orange fluorescence filter with a 586 central length and a 20 nm bandwidth to a first CCD camera; and
    a sorting mechanism that sorts the silkworm cocoons, putting female silkworm cocoons into a female collecting box, and male silkworm cocoons into a male collecting box.

10. The system of claim 9, wherein the detection mechanism comprises the first charge-coupled device (CCD) camera that detects the optical wavelength emitted by the female silkworm cocoon.

11. The system of claim 9, wherein the green light stimulates the female silkworm cocoon to emit an orange 586 nm light, which is transmitted through the dichroic mirror and the orange fluorescence filter and detected by the first CCD camera to identify the female silkworm cocoon.

12. The system of claim 9, wherein images from the first CCD camera are analyzed by an image processing algorithm and database to separate the silkworm cocoons by sex.

13. The system of claim 9, wherein the detection mechanism comprises a second CCD camera that identifies a grid straw cocooning frame plate of the checker cocooning frame, position information for each silkworm cocoon, double cocoons, and inferior cocoons within the grid straw cocooning frame plate.

14. The system of claim 13, wherein the sorting mechanism comprises a plurality of integrated lasers that cut the silkworm cocoons from the checker cocooning frame according to the position information of each silkworm cocoon, so that each male silkworm cocoon goes into the male collecting box and each female silkworm cocoon goes into the female collecting box.

15. The system of claim 13, wherein the sorting mechanism comprises a plurality of electromagnetic hammers that push the silkworm cocoons from the checker cocooning frame according to the position information of each silkworm cocoon, so that each male silkworm cocoon goes into the male collecting box and each female silkworm cocoon goes into the female collecting box.

16. The system of claim 13, wherein the sorting mechanism comprises a female recycling mechanism and a male recycling mechanism, the female recycling mechanism comprising a female recycling winding belt with a cutting device disposed close to the lower surface of the female recycling winding belt that cuts each female cocoon from the female recycling winding belt into the female collecting box, the male recycling mechanism comprising a male recycling winding belt with a cutting device disposed close to the lower surface of the male recycling winding belt that cuts each male cocoon from the male recycling winding belt into the male collecting box.

\* \* \* \* \*